United States Patent [19]

Carlson

[11] Plant 4,678

[45] Mar. 31, 1981

[54] APPLE ROOTSTOCK TREE

[75] Inventor: Robert F. Carlson, Okemos, Mich.

[73] Assignee: Board of Trustees, a Constitutional Corp. operating Michigan State University, East Lansing, Mich.

[21] Appl. No.: 91,070

[22] Filed: Nov. 5, 1979

[51] Int. Cl.[3] ..... A01H 5/00

[52] U.S. Cl. ..... Plt./34

[58] Field of Search ..... Plt./34

*Primary Examiner*—James R. Feyrer

*Attorney, Agent, or Firm*—Ian C. McLeod

[57] ABSTRACT

This apple rootstock originated as a single seedling selected from a group of seedlings obtained from open-pollinated Malling 9 rootstock. It was chosen because of its dwarfing characteristics. It has been increased by vegetative propagation, such as stooling, and by soft- and hard-wood cuttings. Also, this clone is compatible with commercial apple cultivars.

14 Drawing Figures

SUMMARY OF INVENTION

The original plant of this clone came from seed of an open-pollinated Malling 9 (*Malus domestica Boskh*) apple rootstock produced and propagated by Robert F. Carlson, Department of Horticulture, Michigan State University. The seeds were collected October 1958. After stratification and germination, the seedlings were planted in the spring of 1959, and evaluated for growth propensities that summer and fall. Several plants were selected and one of these designated as MAC-9 (MAC=Michigan Apple Clone) was increased by vegetative propagation and used as a rootstock for several cultivars for further testing. MAC-9 was selected mainly for its good dwarfing, precocity, stooling and compatibility characteristics. This rootstock (MAC-9) will be named "Mark".

GENERAL AND DETAILED DESCRIPTION

Since MAC-9 is a clone intended to be used only as a rootstock for apple cultivars, the main detailed description will center on the vegetative parts rather than the flowers and fruits. However, the fruit will be described briefly as another distinctive characteristic. It will be propagated asexually, rather than by seed, in order to maintain clone characteristics.

DESCRIPTION OF VEGETATIVE CHARACTERISTICS

Figure 1:
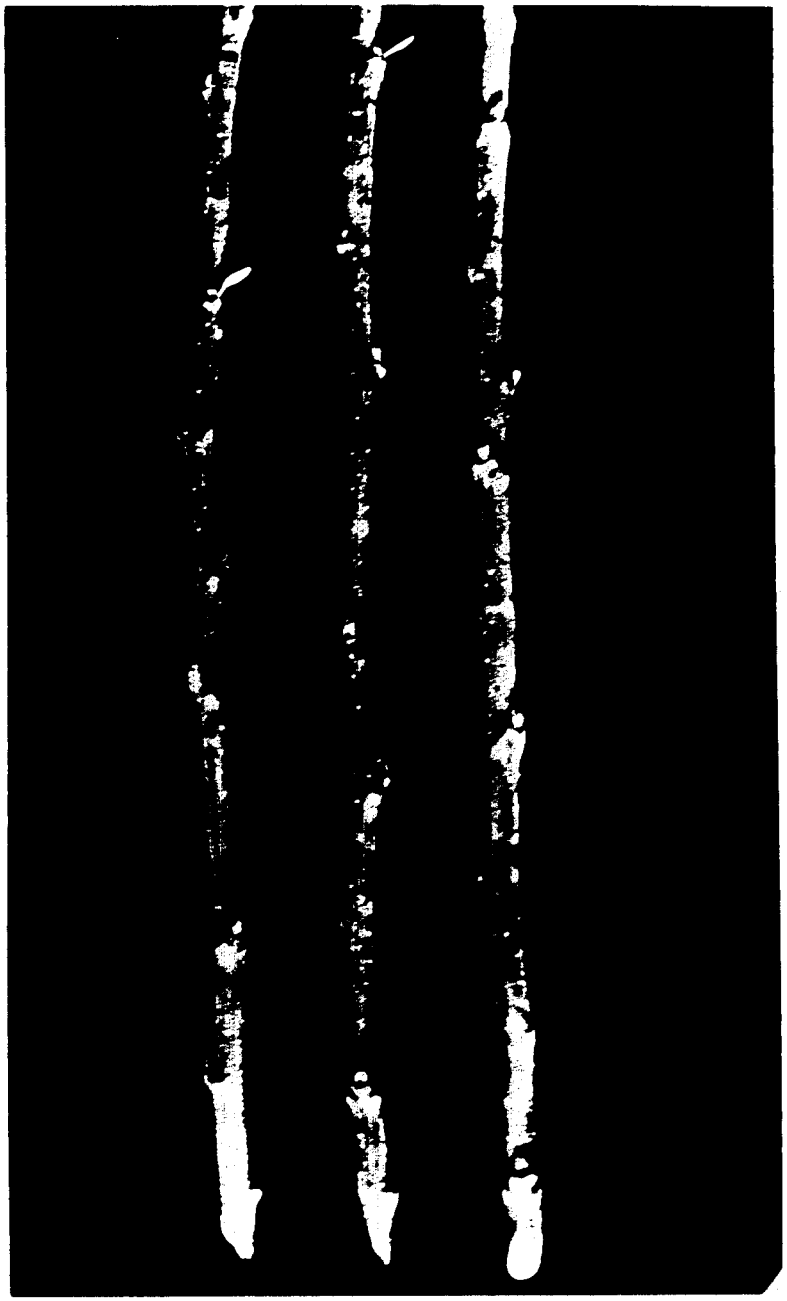
FIG. 1 shows one year old shoots of MAC-9 from which leaves have been removed to show the pubescence (tomentose), the node and internode configuration, the latent buds and the shoulder (bumps) below the leaf scar.
Figure 2:
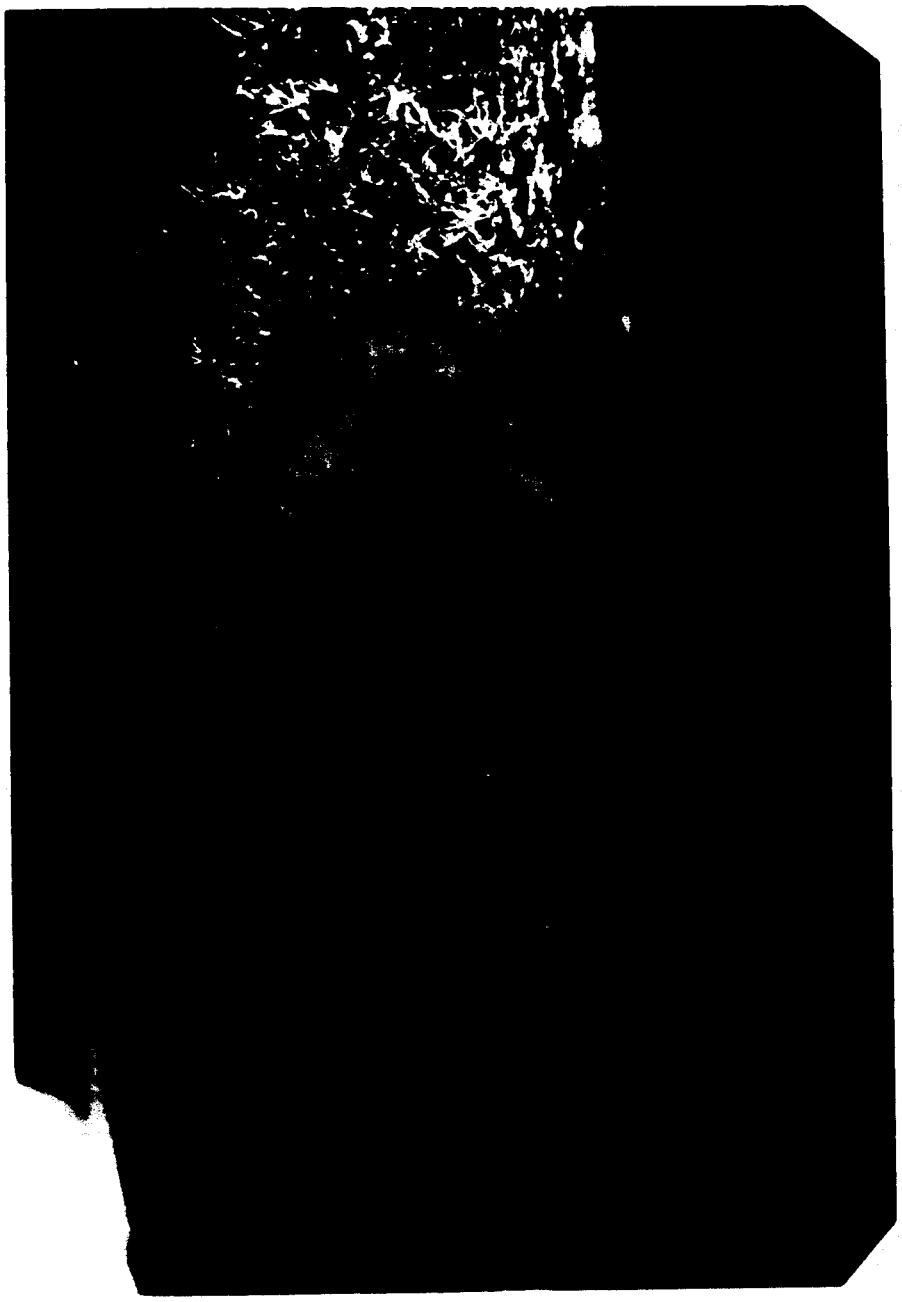
FIG. 2 shows one season's growth of a stem showing tomentose characteristics over the bark and on the bud above the V-shaped bud scar.
Figure 3:
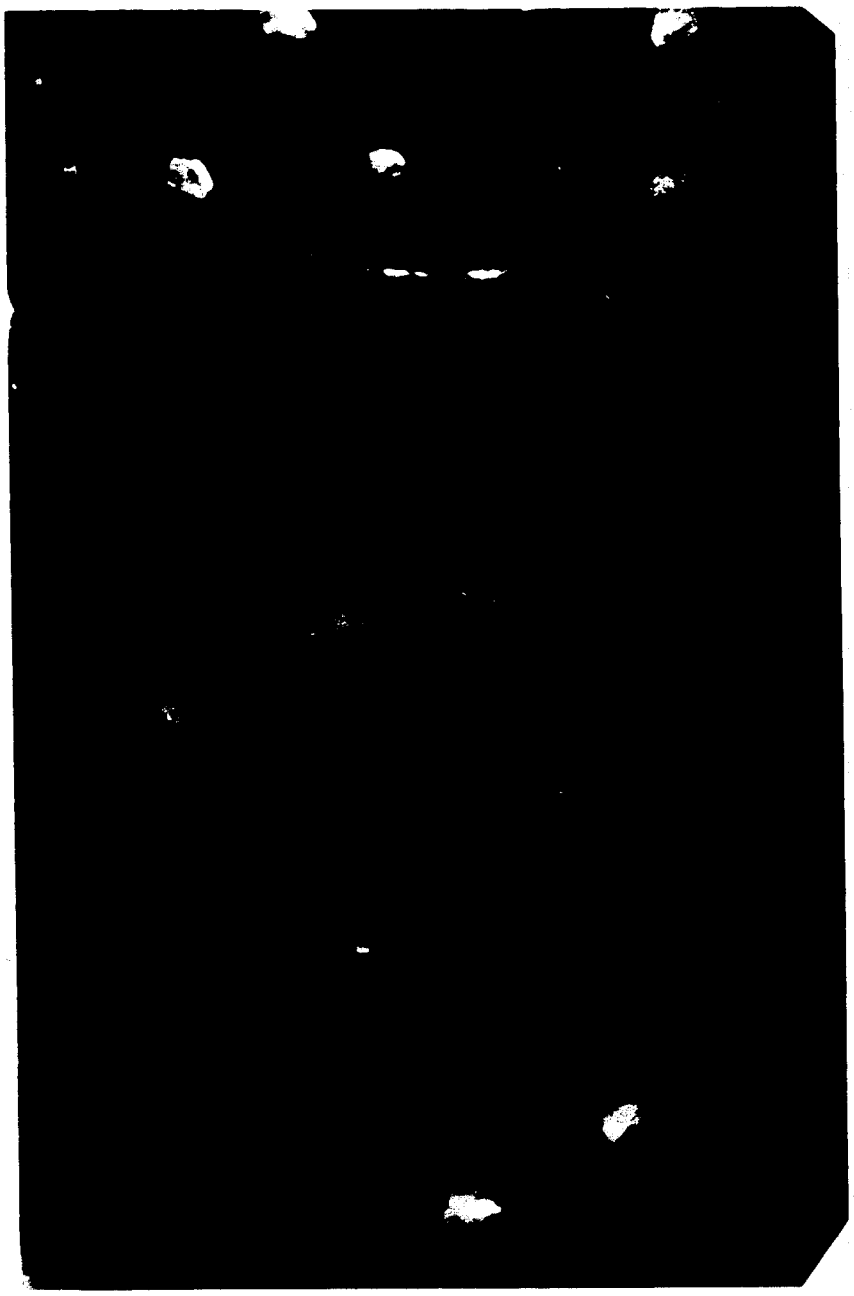
FIG. 3 shows root (stem) showing lenticels, their size and arrangement on the bark surface.

Vegetative shoots: One-year shoots are quite tomentose (fine short hairs); bark gray-brown; lenticels widely spaced, small, inconspicuous, and yellow-white (FIGS. 1, 2 and 3).

Figure 4:
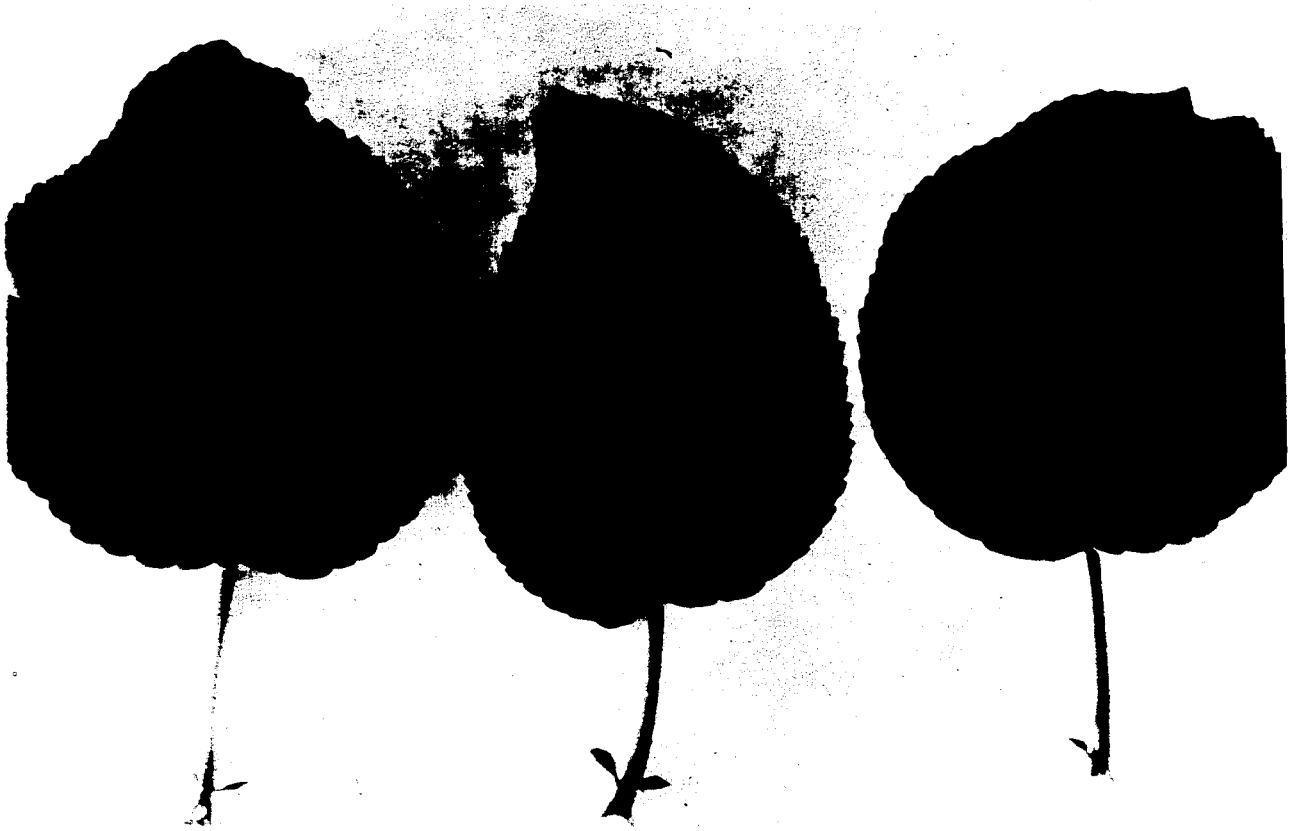
FIG. 4 shows typical leaves of MAC-9 showing the acute serrated margins at sides and more obtuse serrations at the leaf base. The long, slender petiole is slightly grooved, with inconspicuous stipules at the base.
Figure 5:
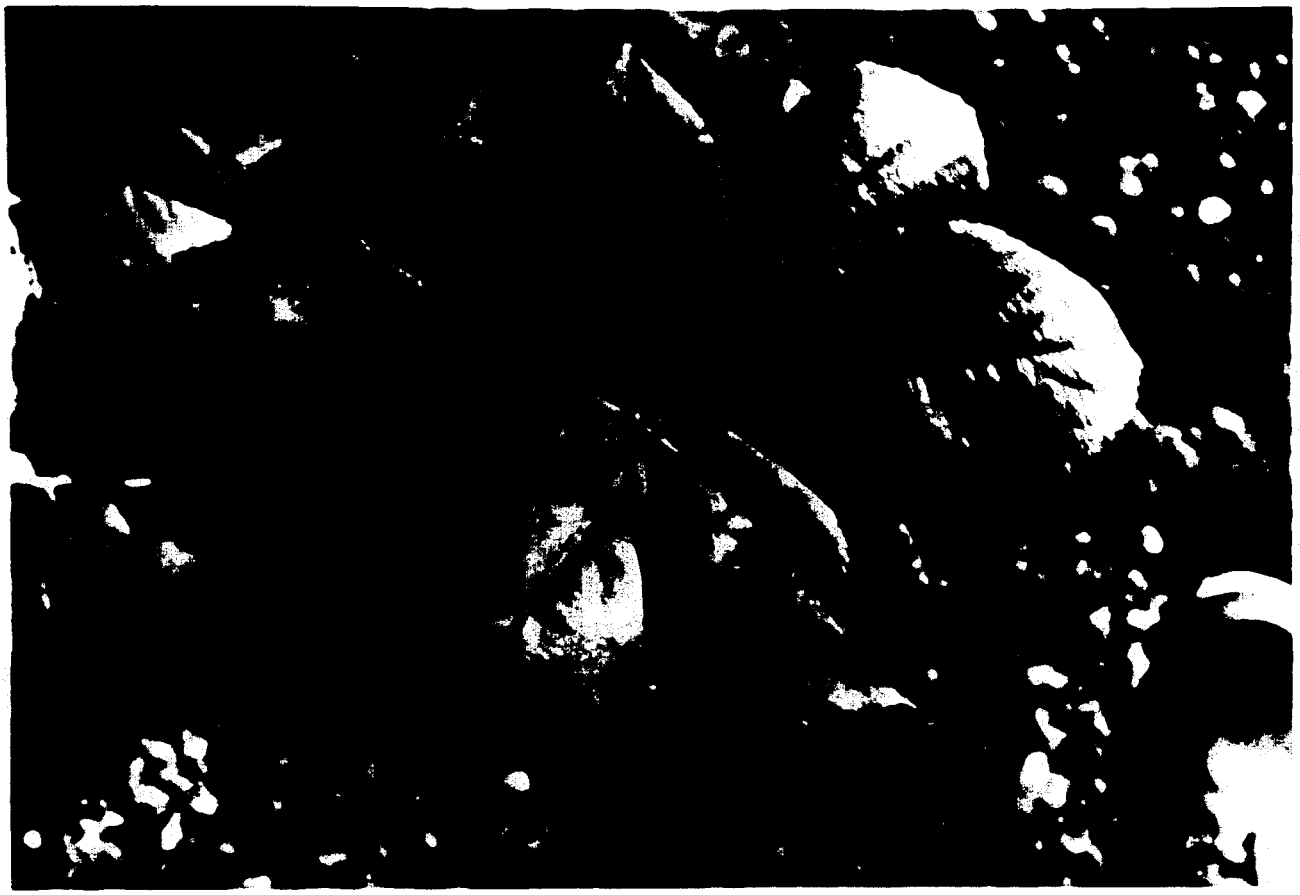
FIG. 5 shows top view of a growing shoot showing typical leaves arranged in phyllotaxical order.

Leaves: Leaves are of average size for apple, averaging 5 cm wide by 7 cm long with uniform saw-tooth serrated margins at the sides and more obtuse margins at the base (FIG. 4). The leaf blade tends to be asymmetric, wavy rather than flat. Leaves are in the normal phyllotaxical ($\frac{2}{5}$) arrangement for the genera (FIG. 5).

Leaf scars: The leaf scars are slightly raised above the stem and form a wide V. They are deep brown (FIG. 2).

Figure 6:
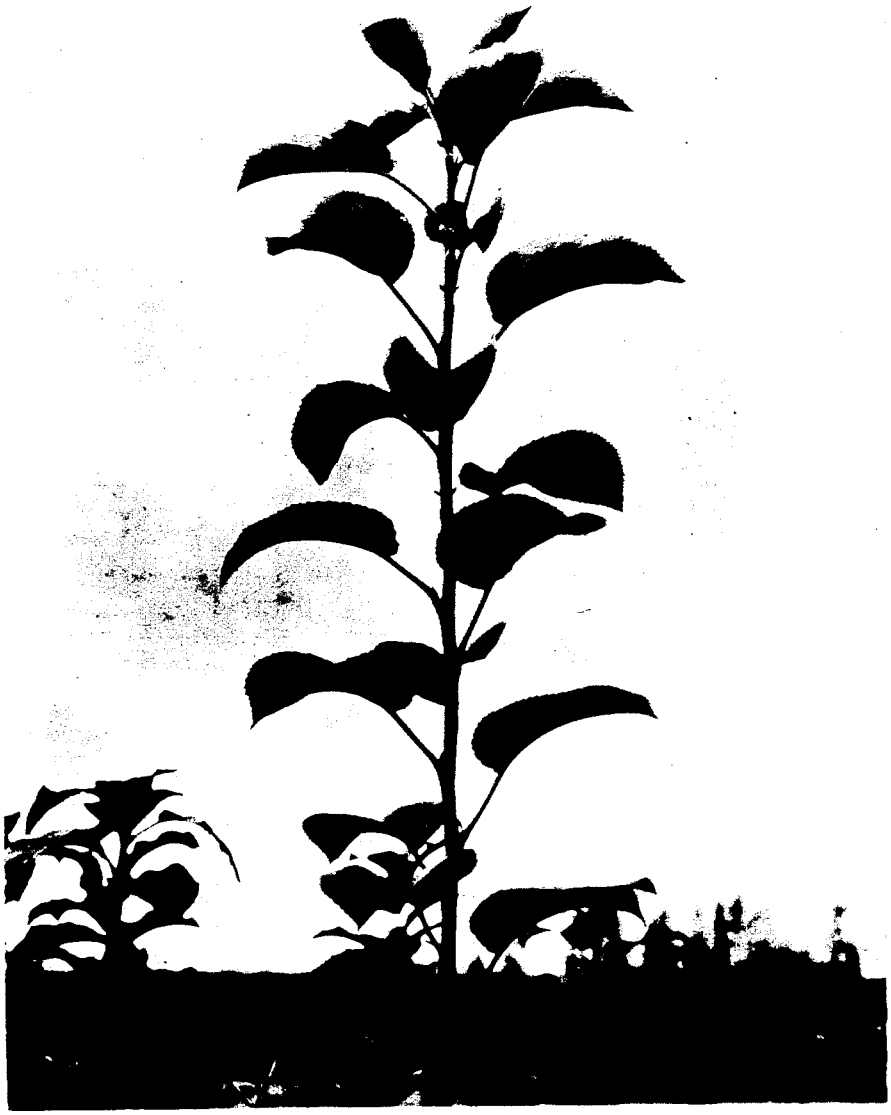
FIG. 6 shows a young shoot from the stoolbed showing the straight stem with slightly cupped leaves and slender petioles.

Petioles (leaf stem): These are slender, long (average 3 cm), slightly channeled or grooved on top, and light reddish brown (FIG. 6).

Stipules (leaf-like structures at base of petiole): These are small and inconspicuous, varying from 3 to 5 mm in length, minutely serrated (FIG. 4).

Figure 7:
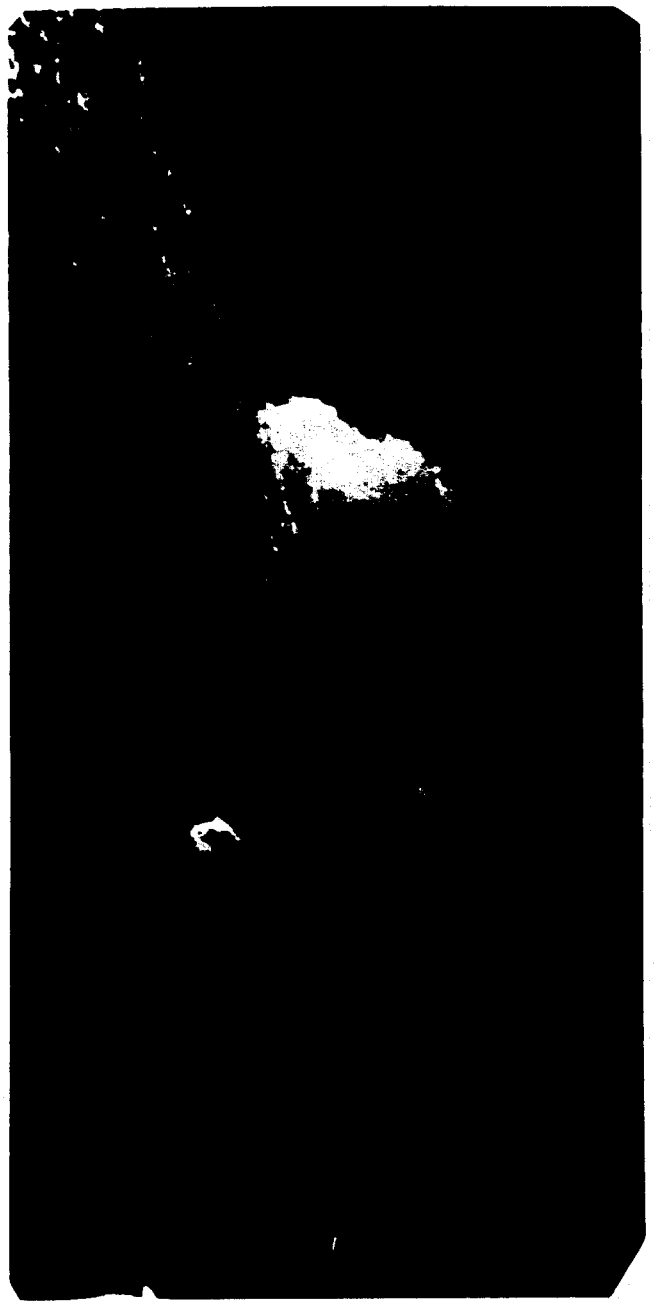
FIG. 7 shows (left) side view of lateral bud above leaf scar, and (right) apical bud at bud break showing the tomentose characteristics.
Figure 7:
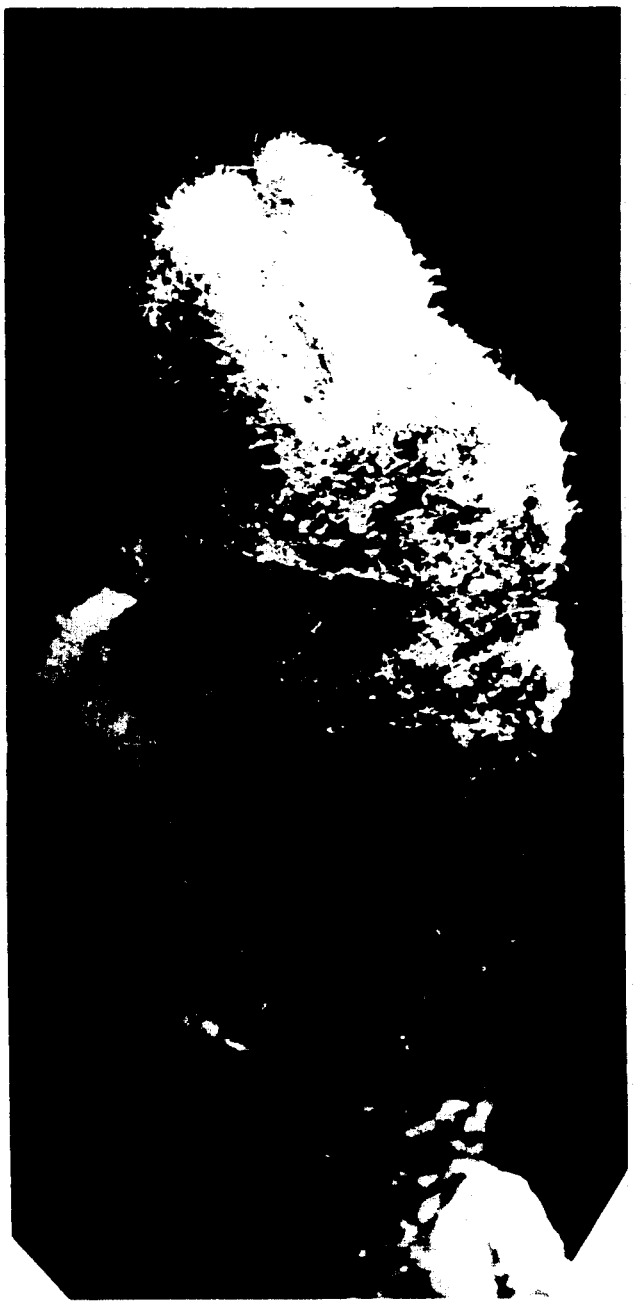

Buds: The dormant buds are small, angular, deep-seated immediately above the leaf scar, with fine white hairs (tomentose) around the bud and the leaf scar. The apical bud is obtuse, larger than the lateral buds, and conspicuously tomentose (FIG. 7).

Dormant Plant Characteristics

Shoots: Stocky, with caliper of one-year old shoots ranging from 5 to 8 mm. Bark is brown to reddish and conspicuously pubescent. The stem (parenchyma and xylem) is rather resilient as compared to M. 9 which is very brittle and breaks easily when bent.

Nodes: Nodes slightly larger in diameter than internodes, with slight shoulder (raised bumps) below and at each side of the leaf scar (FIG. 1).

Internodes: Regularly spaced buds about 25 mm apart on the straight shoot (FIG. 6).

Stooling and Root Characteristics

Figure 8:
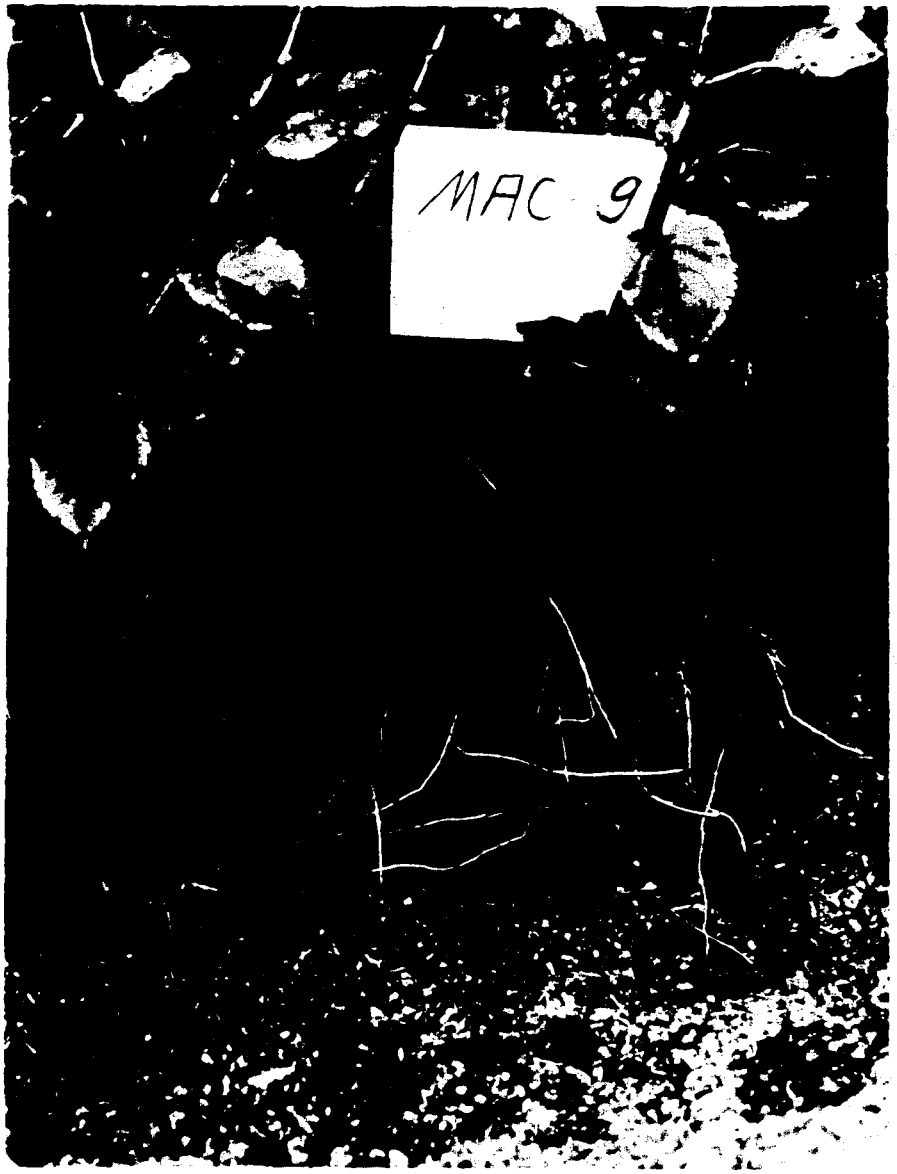
FIG. 8 shows roots of MAC-9 formed in the stoolbed showing typical root growth desirable for rapid propagation of a clone.
Figure 9:
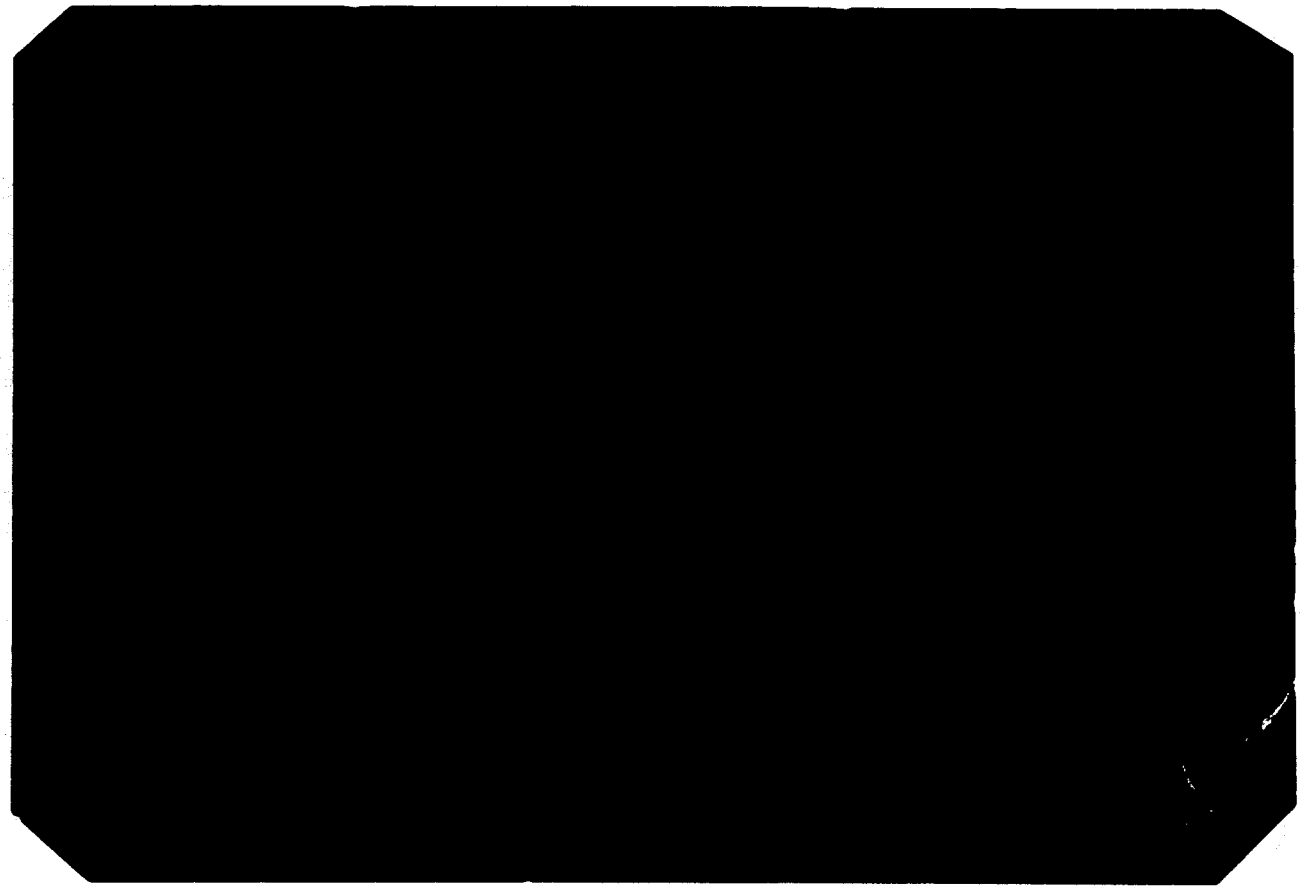
FIG. 9 shows shoots removed from the stoolbed showing roots originating from the nodes.
Figure 10:
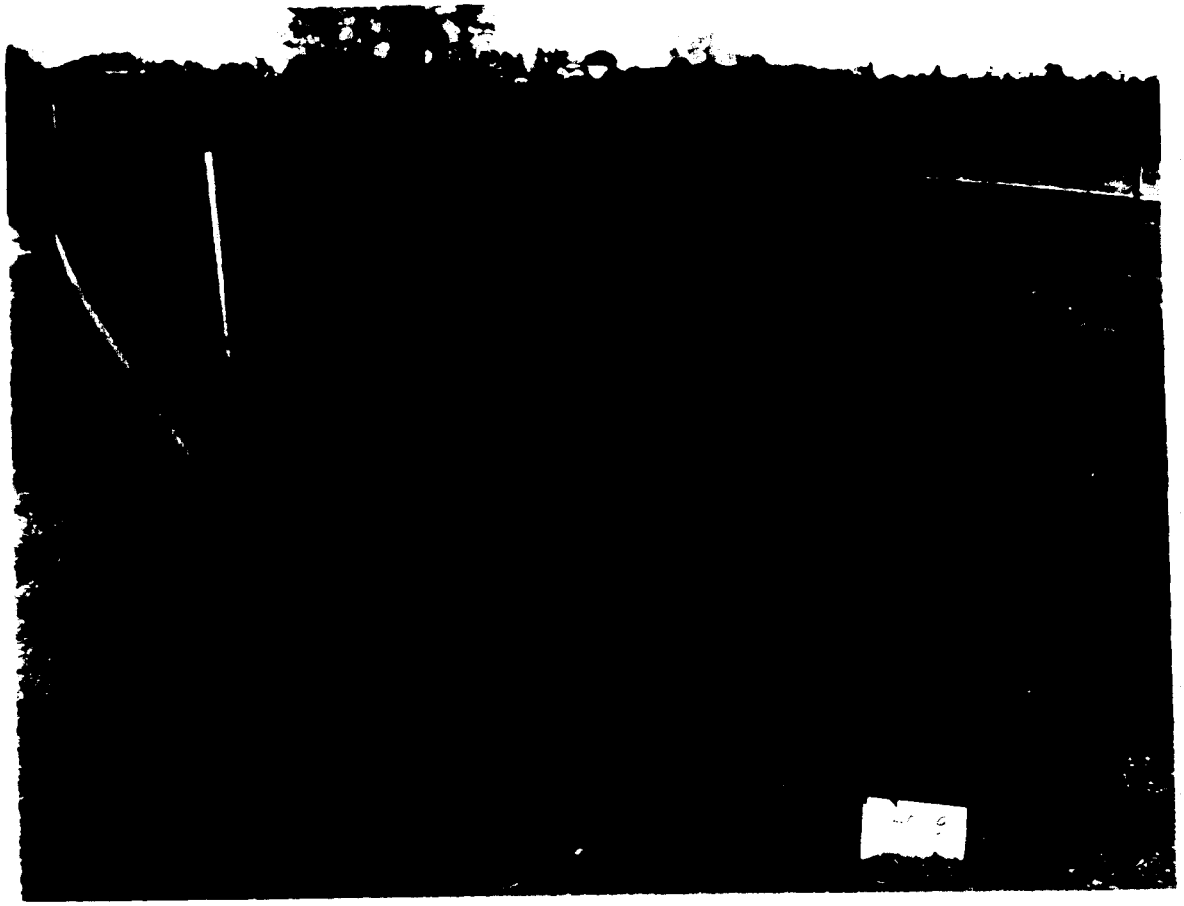
FIG. 10 shows typical growth of MAC-9 in the stoolbed showing the slight outward growth habit of the shoots.

Stooling: MAC-9 reproduces well in stoolbeds, forming strong roots with many sublaterals (FIGS. 8 and 9). Roots form and grow on the mounded shoots during August and through December. Shoots arising from the "stool-crowns" grow slightly outward, but not as much as Malling 9, and production of rooted shoots is similar to that of M. 7 and MM 111. Roots arise mostly at the nodes (FIG. 10).

Flower and Fruit Characteristics

Flowers: Smaller than average for apple cultivars, white with faint reddish streaks toward the base of the petals.

Figure 11:
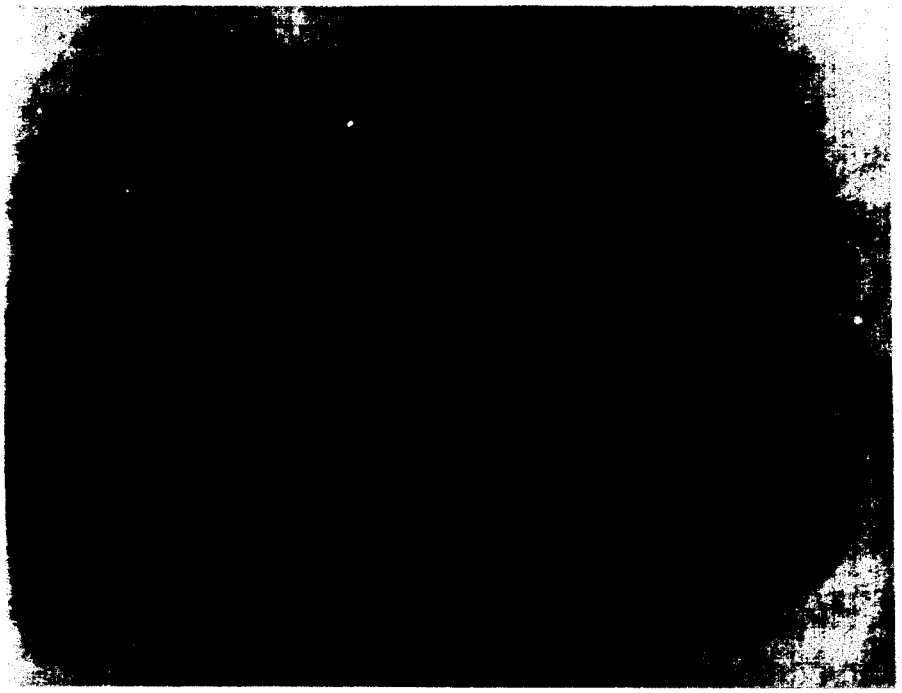
FIG. 11 shows fruit of MAC-9 in longitudinal and cross-section showing the closed calyx cavity and seeds. Fruit red with slight streaking, round to slightly oblong.

Fruit: Round to slightly oblong, red with lighter stripes, about 4 cm in diameter and 5 cm in length; tasteless and of no commercial value, but useful for identification purposes (FIG. 11).

General Characteristics

Figure 12:
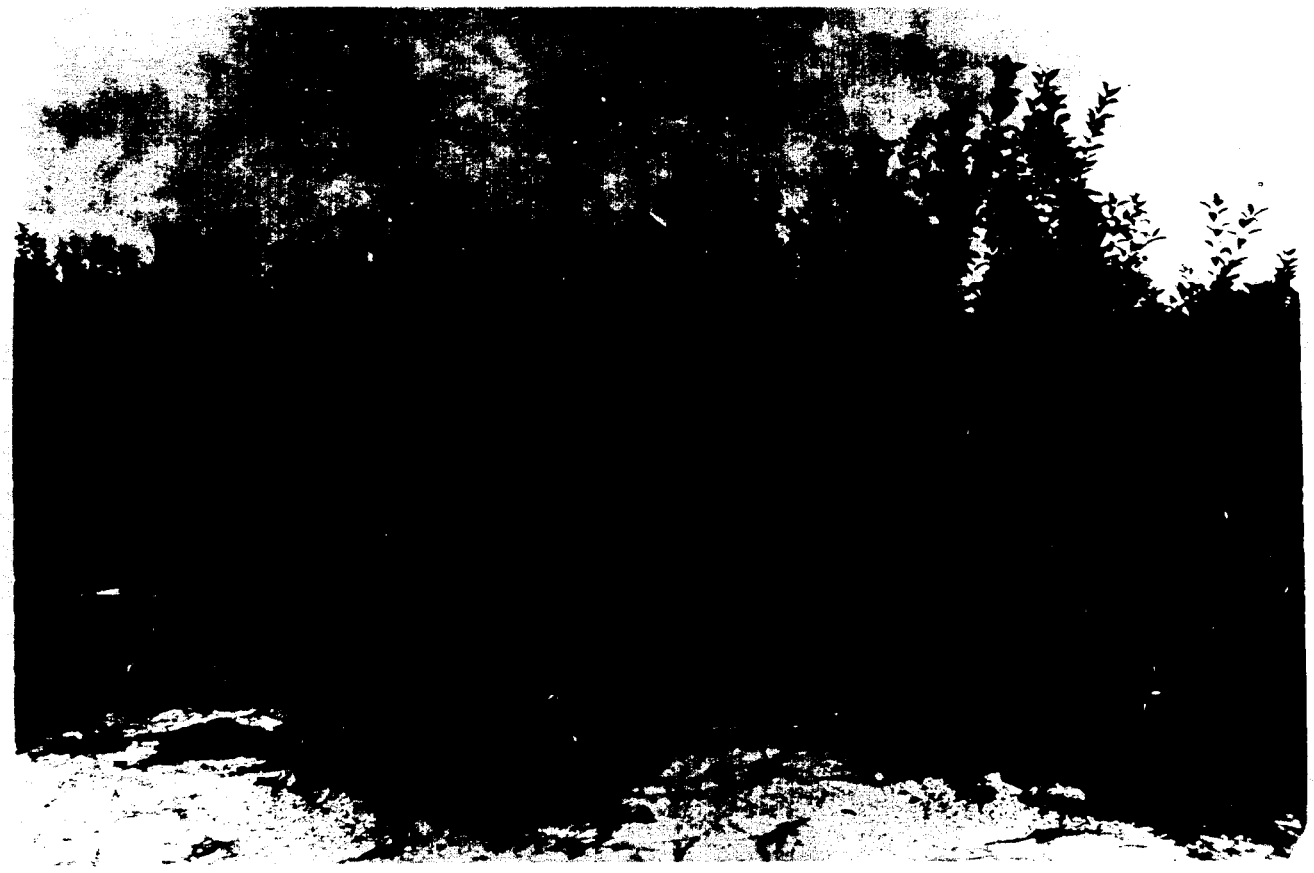
FIG. 12 shows (left) nine year old "Red Prince Delicious" on MAC-9, and (right) same cultivar and same age tree on MAC-5, another vigorous experimental rootstock.

Tree size: Size of trees budded on MAC-9 rootstock will vary somewhat with the vigor of the cultivar and condition of soil and orchard management. Standard "Delicious" is reduced in size about 50% compared to seedling rootstock (FIG. 12). The less vigorous varieties, such as "Jonathan" are more reduced in size when budded on MAC-9.

Dwarfing: MAC-9 rootstock is dwarfing to semi-dwarfing with most apple cultivars.

Figure 13:
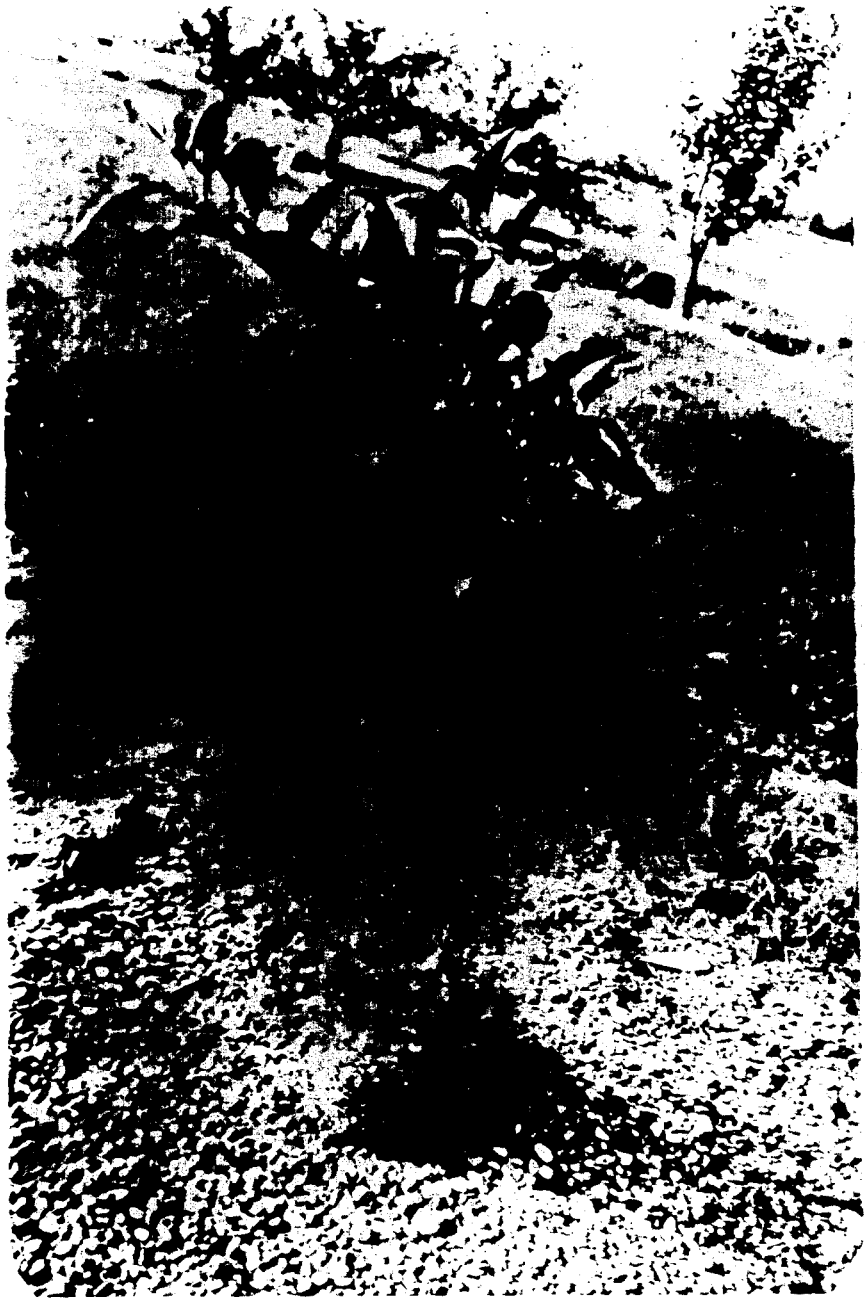
FIG. 13 shows the early bearing characteristics of trees using the MAC-9 rootstock in the second season after the graft union has been made, the first season in the field for the complete tree.

Precocity: Trees on this rootstock often flower and set fruit the first year in the field for the finished tree (FIG. 13), and tend to bear every year.

Figure 14:
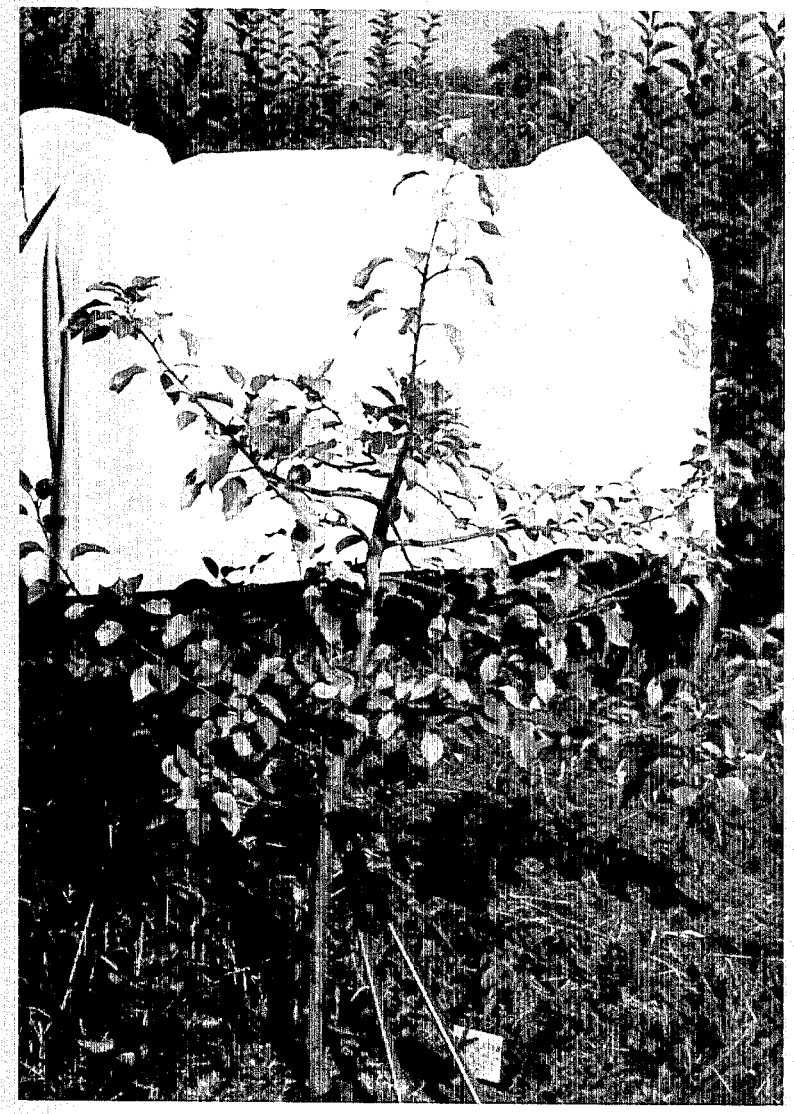
FIG. 14 shows a mature MAC-9 rootstock in September.

Mature tree: The mature MAC-9 tree is dwarfed (FIG. 14). The bark color and smoothness is characteristic. The apple cultivars are budded on the rootstock from the stoolbed and thus the mature plant is not usually seen.

The descriptions here given of MAC-9 rootstock may vary slightly when grown under climatic conditions different from those prevailing in Michigan.

I claim:

1. A new and distinct variety of apple tree referred to by the cultivar name MAC-9 and substantially as herein shown and described characterized particularly by its improved ability to serve as a rootstock for grafting of apple tree cultivars to produce dwarf or semi-dwarf apple trees which are early bearing, have a strong graft and have a well anchored root system without root shoots.

* * * * *